United States Patent [19]

Morineau et al.

[11] Patent Number: 5,065,421
[45] Date of Patent: Nov. 12, 1991

[54] DEVICE FOR MEASURING FLUID FLOWS THROUGH A POROUS BODY

[75] Inventors: Yves Morineau, Morlaas; Rino Begani, Montardon, both of France

[73] Assignee: Societe Nationale Elf Aquitaine (Production), Courbevoie, France

[21] Appl. No.: 442,579

[22] Filed: Nov. 29, 1989

[30] Foreign Application Priority Data

Nov. 30, 1988 [FR] France .................. 88 15661

[51] Int. Cl.5 .......................... G01N 15/10
[52] U.S. Cl. ........................ 378/208; 73/38
[58] Field of Search ........... 378/208, 68, 204, 210; 73/38

[56] References Cited

U.S. PATENT DOCUMENTS

| 4,710,948 | 12/1987 | Withjack | 378/208 |
| 4,753,107 | 6/1988 | Reed et al. | 73/38 |
| 4,827,761 | 5/1989 | Vinegar et al. | 378/208 |

FOREIGN PATENT DOCUMENTS 2185114  7/1987  United Kingdom ............ 73/38

Primary Examiner—Carolyn E. Fields
Attorney, Agent, or Firm—Oblon, Spivak, McClelland, Maier & Neustadt

[57] ABSTRACT

Device for measuring by gammagraphy fluid flows, in particular in drilling cores of porous media originating from oil fields, said device being used under field conditions. The device comprises a tubular body, the outer part of which is permeable to radiation, and which is held between tie rods, and a piston at one end, the sample being placed at the other end inside a flexible sleeve between the piston and a fixed support. The lateral wall of the tubular body is lined with a thin inner metal liner permeable to radiation.

10 Claims, 1 Drawing Sheet

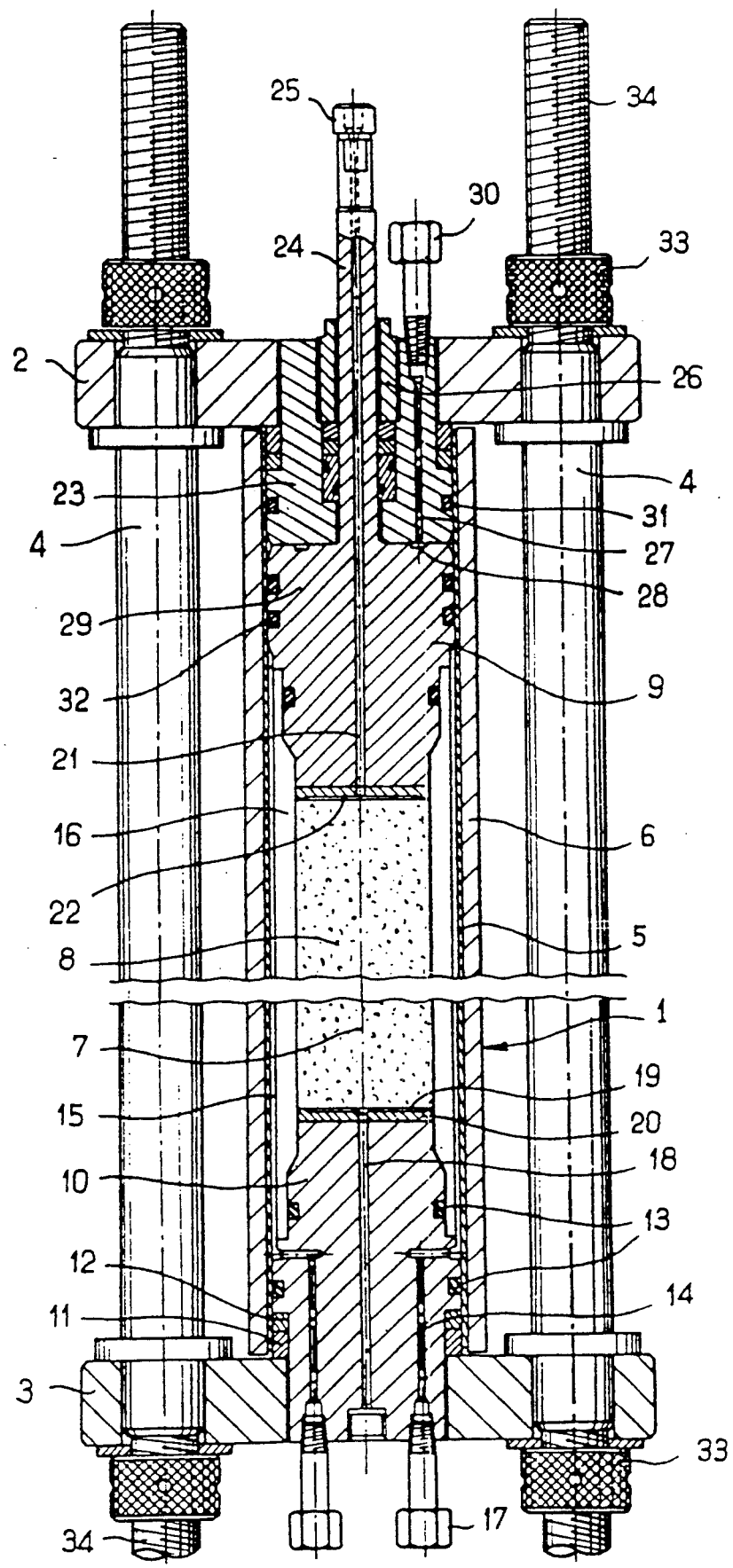

DEVICE FOR MEASURING FLUID FLOWS THROUGH A POROUS BODY

BACKGROUND OF THE INVENTION

1. Field of the Invention

The present invention relates to a device for measuring fluid flows through a porous body and, more particularly, through drilling cores of porous media originating from oil fields.

2. Discussion of the Background

In order to assess the performance of the various production mechanisms on a microscopic scale and to determine the quantitative parameters intended to supply the numerical production forecasting models, the current procedure is to run a fluid or displace several fluids in the drilling cores.

Devices for creating flows of fluid through drilling cores or samples have been known for a very long time. Reference may be made usefully to the article of G. L. Hassler, R. R. Rice and E. H. Leeman, entitled "Investigation on the recovery of oil from sandstone by gas-drive" (Trans. Aime. Vol. 118, page 116, 1936).

Less and less use is being made of the measuring devices comprising a plastic flow cell, usually used under "laboratory conditions", in favour of devices comprising a steel cell, the thickness of which makes it possible to withstand pressures of several hundreds of bars, at temperatures which may exceed 150° C. In these latter devices, real samples or drilling cores are arranged in the cell and real fluids coming from the oil field are used. Production mechanisms may therefore be studied under real field conditions.

However, these devices, at the very least those which are used under "field conditions" because they make use of real fluids and drilling cores, make it possible only to assess the performance of the mechanisms studied on the basis of material balances between what is initially in the drilling core studied, what is injected therein and what is produced.

In fact, it is not possible to determine what is produced inside the drilling core, between the point of injection and the point of production In particular, nothing is known about local saturation distributions, about the form and deformation of displacement fronts which may be generated by heterogeneities or mobility ratios of unfavourable fluids or any other causes. This makes many interpretations risky and sometimes even impossible.

In order to monitor the flows within drilling cores, increasing use is being made, in measuring devices working under laboratory conditions with plastic cells, of gammagraphy, that it is to say measurement of the attenuation of an X or gamma ray by the material penetrated, attenuation which is a function of the density of the elements encountered.

As the metal cells of measuring devices under field conditions are not sufficiently transparent to X or gamma rays, it is proposed to replace the metal cell with a much less absorbent composite cell.

A cell of this type is described in GB-A-2,185,114. Said cell, intended for working with a scanner, was designed without piston tie rods, so as to be transparent at an angle of 360 degrees. It is produced by windings of filaments constructed of carbon fibres coated with resin, which winding is effected at two different angles so that the cell which is thus made of two layers, an inner and an outer layer, can withstand radial and axial pressures.

The device described in this patent has drawbacks even though it represents a substantial advance compared with prior measuring devices. In the first place the working life and efficiency of a layer constructed of a carbon fibre- and resin-based composite are lower than those of metal cells, because of the forces to which said layer is subjected, despite the fact that it may be very thick.

In the second place, mention should be made of the difficulties associated with leakproofness. An internal leakproof lining of elastomer fibre is used. It is known that the efficiency and working life of said lining are problematic, as well as installation thereof. Furthermore, said lining does not make it possible to have metal surfaces adjusted to the conventional standards in order to accept conventional O-ring seals. It is therefore necessary to install complex sealing joints between the cell body and the pistons, which, in addition to the disadvantages associated with doubtful reliability, prohibits any flexibility in the choice of the length of the rock sample to be studied.

SUMMARY OF THE INVENTION

Accordingly, one object of the present invention is to overcome the abovementioned drawbacks and the subject of the present invention is a measuring device capable of being used in gammagraphy and under field conditions and designed to work with a more modest gammagraphy device, that is to say a lower transparency angle, for example 140°.

To this end, the measuring device according to the invention is of the type comprising a tubular body in two parts, the outer part of which is permeable to at least one radiation and is held between tie rods, at least one piston at least part of which is introduced at one end of the said body, a fixed sample support arranged at the other end of the said body, a flexible sleeve arranged inside the said tubular body, the said sample being arranged in the said sleeve and between the piston and the support, and means of injection of at least one fluid at at least one end and through the said sample, and it is characterized in that the lateral wall of the said tubular body is lined with a thin inner metal liner permeable to the said radiation.

One advantage of the present invention lies in the fact that the metal liner makes it possible to ensure that the composite tubular body is impervious to all fluids, liquids or gases, at elevated pressures, on the one hand, and allows the piston to be displaced within the tubular body while ensuring leakproofness between the said piston and tubular body by insertion of sealing joints mounted according to conventional standards, on the other hand.

Another advantage is that the tubular body may be designed so as to withstand only radial stresses, the tie rods equipped with buffers receiving the longitudinal stresses, which makes it possible not to make the outer layer of the tubular body too thick. As a result, it may be made very light and transparent to X or gamma rays.

Another advantage is that putting the pistons down releases the cell body completely, making it extremely easy to position the drilling core.

Yet another advantage is that the length of the cell may be adapted to the requirements of the experiment by means of the availability of several interchangeable composite tubular bodies and pairs of suitable tie rods.

BRIEF DESCRIPTION OF THE DRAWING

Other advantages and features will emerge more clearly from reading the description of an embodiment according to the invention, and from the attached drawing wherein The FIGURE is a longitudinal sectional view of the device according to the invention.

DESCRIPTION OF THE PREFERRED EMBODIMENT

The device comprises a tubular body 1 arranged between two flanges 2 and 3 which are connected by two tie rods 4.

The tubular body 1 is constructed of a thin inner metal liner 5 having an external casing 6 which is produced from carbon filaments impregnated with resin of the epoxy type, and wound onto the inner liner 5 at an angle of approximately 80°, relative to the longitudinal axis 7 of the said tubular body 1. The winding changes direction at each end, so as to obtain filaments which interlace from one layer to another in the external casing 6.

Inside the tubular body 1 there is arranged a porous body to be tested 8, for example a drilling core originating from an oil field. On either side of the drilling core 8 there are arranged two pistons 9 and 10, one of which, 9, is movable and the other, 10, secured in the tubular body 1, the fixed piston 10 in fact forming an entry plug. The entry plug 10 is fastened to the flange 3 by means of a washer 11 and comprises a joint 12 mounted on the washer 1 and O-ring seals 13. One or more bores 14 are provided in the entry plug 10 and open into an annular space 15 provided between the inner liner 5 and a membrane 16, for example of rubber in the form of a triple sleeve, which encases the drilling core 8 and which is secured between and on the movable piston 9 and the entry plug 10. Joining pieces 17 connect a fluid source, not shown, with the bores 14, it being possible, for the fluid to be, for example, the water which is used to press the membrane 16 against the drilling core 8. A central bore 18 is also provided in the entry plug 10 in order to enable an injection of a production fluid or fluids of the oil field into the drilling core 8 by means of grooves 19 provided on the surface 20 of the entry plug 10 or on an intermediate piece mounted between the drilling core 8 and the entry plug 10.

The movable piston 9 also comprises a central bore 21 for the injection of production fluids, for example, into the drilling core 8, by means of grooves 22. A plug 23 is mounted under the movable piston 9 and is secured on the flange 2 by a joint 12 and a washer 11, the said plug 23 being penetrated by a rod 24 of the movable piston 9, and provided with a joining piece 25. A gland screw 26 is penetrated by the piston rod 24 and rests on a shoulder of the plug 23, with insertion of washer and sealing joints therebetween. A bore 27 is provided in the plug 23 and connects, by means of a connecting piece 30, a source of fluid under pressure and not shown, with an annular groove 28 provided on the adjacent surface 29 of the movable piston 9, so as to allow the longitudinal stressing of the drilling core 8. O-ring seals 31 and 32 ensure the leakproofness respectively of the plug 23 and the movable piston 9 in relation to the inner liner 5.

Finally, knurled nuts 33 are mounted on threaded parts 34 of the tie rods 4 and make it possible to adjust the measuring device to the length of the measuring cell which is mainly constructed of the tubular body 1.

In a preferred embodiment of the invention, the inner liner 5 is made of aluminium, and is 1 mm thick, which does not present an obstacle to transmission of gamma radiation and, namely because of the low coefficient of absorption which is approximately 4 times less than that of steel and because of its thinness Experiments carried out with the device according to the invention have made it possible to determine that the test pressure was of the order of 600 bars with a working pressure of the order of 400 bars, the calculated bursting pressure being 2200 bars, whereas the working temperature was approximately 110° C.

It is also possible to construct the inner liner 5 of steel provided that the thickness is reduced in order to make it transparent to gamma rays, for example. A suitable chosen thickness of the inner steel liner 5 is between 1/10 and 5/10 mm.

A method for the production of the tubular body 1 consists, in a first stage, in winding the carbon filaments which are bonded by a suitable epoxy resin, around an aluminium mandrel, until the desired thickness is obtained for the composite outer layer designated by the reference 6 in the FIGURE. The winding of the carbon filaments is effected at an angle which, preferably, is less than 90° and, for example, between 60° and 80°. Furthermore, at each end of the mandrel, the winding changes direction so that two adjacent layers produced around the mandrel have carbon filaments which are interlaced.

In a second stage, the aluminium mandrel is drilled until an inner liner is obtained having a thickness of approximately 1 mm. After this, if necessary, the internal wall of the inner liner is adjusted in order to enable correct positioning of the plugs and piston with their sealing joints, as has been described above.

In an exemplary embodiment giving excellent results, the composite layer 6 has a thickness substantially equal to 7.5 cm, and the tubular body a length of 123 cm, with an internal diameter of the liner of 6.9 cm.

The tubular body 1 obtained according to the method of the invention has the great advantage of avoiding an internal composite liner which, generally, is not fluid-, liquid- or gas-tight, and which offers said fluids a certain permeability resulting in leaks by "beading".

The device according to the invention operates in the same manner as prior devices, with the difference that, when it is desired to subject the drilling core to longitudinal stress, a suitable fluid is introduced into the bore 27, which, by exerting a pressure on the surface 29 of the piston 9, displaces the latter in the tubular body by a suitable travel so as to create the desired longitudinal stress.

We claim:

1. A device for measuring fluid flows through a porous sample, comprising:
   a tubular body having an external casing permeable to gamma radiation, said tubular body being held between tie rods;
   a piston, at least part of which is received within a first end of said tubular body;
   a fixed sample support received within a second end of said tubular body;
   a flexible sleeve arranged inside said tubular body;
   a receiving space for receiving the sample formed within said sleeve between the piston and the support; and
   means for injecting fluid through the sample at at least one of said first and second ends of the tubular body, wherein the external casing of said tubular body is lined with an inner metal liner having a thickness permeable to said gamma radiation.

2. The device according to claim 1, wherein the inner metal liner is made of aluminum.

3. The device according to claim 2, wherein the inner metal liner is approximately 1 mm thick.

4. The device according to claim 1, wherein the inner metal liner is made of steel and is between one-tenth and five-tenth of a millimeter thick.

5. The device according to claim 1, wherein the external casing comprises a winding of filaments bonded by a resin, wherein the filaments are wound at an angle of 80°.

6. The device according to claim 1, wherein the piston is slideably received within the tubular body.

7. The device according to claim 1, wherein a plug is arranged on the surface of the piston which is opposite to that in contact with the sample, the said plug being equipped with a passage for a fluid for longitudinal compression of the piston, the said passage opening into an annular groove provided in the surface of the piston opposite the said plug.

8. A method for the production of a tubular body permeable to gamma radiation, comprising the steps of:
 winding filaments on a metal mandrel or on a tube to an appropriate thickness; and
 boring the mandrel or the tube over its entire length until an inner liner is obtained having a thickness permeable to gamma radiation.

9. The method according to claim 8, wherein said step of winding filaments includes the substeps of:
 winding the filaments in layers at an angle of approximately 30°; and
 alternating the direction of winding from one layer to another.

10. Method according to claim 8, wherein the step of boring the mandrel or tube comprises the substeps of:
 boring a mandrel or tube made of aluminum; and
 carrying out the boring until an inner liner is obtained having a thickness of approximately one millimeter.

* * * * *